(12) United States Patent
Dhanoa et al.

(10) Patent No.: US 6,506,784 B1
(45) Date of Patent: Jan. 14, 2003

(54) USE OF 1,3-SUBSTITUTED PYRAZOL-5-YL SULFONATES AS PESTICIDES

(75) Inventors: Daljit S. Dhanoa, West Chester, PA (US); Dario Doller, Branford, CT (US); Sanath Meegalla, Devon, PA (US); Richard M. Soll, Lawrenceville, NJ (US); Dimitris Agrafiotis, Downingtown, PA (US); Nancy Wisnewski, Fort Collins, CO (US); Gary M. Silver, Fort Collins, CO (US); Dan T. Stinchcomb, Fort Collins, CO (US); R. Lee Seward, Eaton, CO (US)

(73) Assignees: 3-Dimensional Pharmaceuticals, Inc., Exton, PA (US); Heska Corporation, Fort Collins, CO (US)

(*) Notice: Subject to any disclaimer, the term of this patent is extended or adjusted under 35 U.S.C. 154(b) by 3 days.

(21) Appl. No.: 09/606,986

(22) Filed: Jun. 29, 2000

Related U.S. Application Data

(60) Provisional application No. 60/141,849, filed on Jul. 1, 1999.

(51) Int. Cl.⁷ .................................................. A01N 43/56
(52) U.S. Cl. .................................... 514/407; 548/370.4
(58) Field of Search .......................................... 514/407

(56) References Cited

U.S. PATENT DOCUMENTS

| | | |
|---|---|---|
| 1,685,407 A | 9/1928 | Mannich |
| 3,235,360 A | 2/1966 | Soboczenski |
| 3,326,662 A | 6/1967 | Toyosato et al. |
| 3,364,227 A | 1/1968 | Robinson |
| 3,637,738 A | 1/1972 | Gschwend et al. |
| 3,818,026 A | 6/1974 | Boesch |
| 3,836,539 A | 9/1974 | Boesch |
| 3,846,440 A | 11/1974 | Boesch et al. |
| 3,883,550 A | 5/1975 | Goddard |
| 4,059,434 A | 11/1977 | Wolf |
| 4,108,628 A | 8/1978 | Wolf |
| 4,111,681 A | 9/1978 | Goddard |
| 4,124,373 A | 11/1978 | Wolf |
| 4,331,678 A | 5/1982 | De'Ath et al. |
| 4,666,507 A | 5/1987 | Yanagi et al. |
| 4,695,312 A | 9/1987 | Hayase et al. |
| 4,740,231 A | 4/1988 | Gehring et al. |
| 5,104,994 A | 4/1992 | Roberts et al. |
| 5,134,155 A | 7/1992 | Connolly et al. |
| 5,232,940 A | 8/1993 | Hatton et al. |
| 5,306,694 A | 4/1994 | Phillips et al. |
| 5,387,693 A | 2/1995 | Connolly et al. |
| 5,487,976 A | 1/1996 | Soderlund et al. |
| 5,637,607 A | 6/1997 | Pilato et al. |
| 5,707,936 A | 1/1998 | Oberdorf et al. |
| 5,814,652 A | 9/1998 | Wu |
| 5,849,778 A | 12/1998 | Heil et al. |
| 5,869,517 A | 2/1999 | Müller et al. |
| 6,069,157 A | 5/2000 | Banks |

FOREIGN PATENT DOCUMENTS

| | | |
|---|---|---|
| DE | 19511269 A1 | 10/1995 |
| DE | 19518054 A1 | 9/1996 |
| DE | 19544799 A1 | 6/1997 |
| DE | 197 56 115 A1 | 6/1999 |
| EP | 0 138 527 A2 | 4/1985 |
| EP | 0 234 119 A1 | 9/1987 |
| EP | 0 350 311 A1 | 1/1990 |
| EP | 0 392 499 A2 | 10/1990 |
| EP | 0 398 499 A2 | 11/1990 |
| EP | 0 412 849 A2 | 2/1991 |
| EP | 0 418 016 A1 | 3/1991 |
| EP | 0 558 999 A2 | 9/1993 |
| EP | 0 659 745 A1 | 6/1995 |
| EP | 0 152 286 A1 | 8/1995 |
| EP | 1 745 684 A1 | 12/1996 |
| EP | 0 846 686 A1 | 6/1998 |
| FR | 2301250 | 10/1976 |
| JP | 59181259 | 10/1984 |
| JP | 6041667 | 3/1985 |
| JP | 60-233061 | 11/1985 |
| JP | 61-165373 | 7/1986 |
| JP | 63-287766 | 11/1988 |
| JP | 8208620 | 8/1996 |
| KR | 917886 | 10/1991 |
| WO | WO 92/13451 | 8/1992 |
| WO | WO 93/06089 | 4/1993 |
| WO | WO 93/19054 | 9/1993 |
| WO | WO 93/21160 | 10/1993 |
| WO | WO 94/13643 | 6/1994 |
| WO | WO 94/13644 | 6/1994 |
| WO | WO 94/13661 | 6/1994 |
| WO | WO 94/13677 | 6/1994 |
| WO | WO 94/21606 | 9/1994 |
| WO | WO 95/22530 | 8/1995 |
| WO | WO 95/33727 | 12/1995 |
| WO | WO 98/22442 A2 | 5/1998 |

OTHER PUBLICATIONS

Cole, L.M. et al., "Action of Phenylpyrazole Insecticides at the GABA–Gated Chloride Channel," *Pesticide Biochem. Biophys.* 46:47–54 Academic Press, New York, NY (1993).

(List continued on next page.)

*Primary Examiner*—Robert W. Ramsuer
(74) *Attorney, Agent, or Firm*—Sterne, Kessler, Goldstein & Fox P.L.L.C.

(57) ABSTRACT

The present invention is directed to inhibiting pest GABA receptors by contacting said receptors with a compound of Formula I:

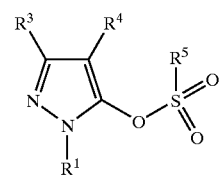

The invention is also directed to methods of controlling pests, especially insects and arachnids such as fleas and ticks, and to novel compounds within the scope of Formula I.

17 Claims, No Drawings

OTHER PUBLICATIONS

Finkelstein, B.L. and C.J. Strock, "Synthesis and Insecticidal Activity of Novel Pyrazole Methanesulfonates," *Pestic. Sci. 50*:324–328 John Wiley & Sons, New York, NY (1997).

Dialog File 351, Accession No. 4146500, Derwent WPI English language abstract for JP 59181259 (Document AL1). (No date available).

Dialog File 351, Accession No. 4264102, Derwent WPI English language abstract for JP 6041667 (Document AM1). (No date available).

Dialog File 351, Accession No. 9260868, Derwent WPI English language abstract for KR 917886 (Document AO2). (No date available).

Dialog File 351, Accession No. 10324917, Derwent WPI English language abstract for EP 0 659 745 A1 (Document AM4). (No date available).

Dialog File 351, Accession No. 10392384, Derwent WPI English language abstract for WO 95/22530 (Document AN4). (No date available).

Dialog File 351, Accession No. 10451076, Derwent WPI English language abstract for DE 19511269 A1 (Document AO4). (No date available).

Dialog File 351, Accession No. 10925014, Derwent WPI English language abstract for JP 8208620 (Document AP4). (No date available).

Dialog File 351, Accession No. 10916684, Derwent WPI English language abstract for DE 19518054 A1 (Document AL5). (No date available).

Dialog File 351, Accession No. 11321362, Derwent WPI English language abstract for DE 19544799 A1 (Document AM5). (No date available).

Ando, I. et al., "Synthesis and Biological Activity of Cyclic Imide Derivatives and Related Compounds," *Agric. Biol. Chem. 53*:2001–2003, Japan Society for Bioscience, Biotechnology and Agrochemistry, Japan (1989).

Baraldi, P.G. et al., "A Mild One–Pot Synthesis of Thieno [3,4–c]pyrazoles and Their Conversion into Pyrazole Analogs of o–Quinodimethane," *Synthesis* (9):1331–1334, Thieme, New York, NY (Sep. 1998).

Bardou, L. et al., "XVI.—Pyrazoles bicycliques," *Bulletin de la Société Chimique de France* (1):289–294, Société Chimique de France, Paris, France (1967).

Bauer, V.J. et al., "Synthesis Alkylation, and Oxidation of Thieno[3,4–c]– and –[3,2–c]pyrazoles," *J. Med. Chem. 14*:454–456, American Chemical Society, Washington, DC (1971).

Chou, T.–s. and Chang, R.–C., "A Novel Route to the Preparation of Pyrazole Analogues of o–Xylylene," *J. Org. Chem. 58*:493–496, American Chemical Society, Washington, DC (1993).

Chou, T.–s. and Chang, R.–C., "Synthesis and Reactions of N–Substituted Pyrazolo–3–Sulfolenes," *Heterocycles 36*:2839–2850, Elsevier Science, New York, NY (1993).

Connolly, P.J. et al., "HMG–CoA Reductase Inhibitors: Design, Synthesis, and Biological Activity of Tetrahydroindazole–Substituted 3,5–Dihydroxy–6–heptenoic Acid Sodium Salts," *J. Med. Chem. 36*:3674–3685, American Chemical Society, Washington, DC (1993).

Duncan, D.C. et al., "The Preparation of N–Carboalkoxypyrazoles and N–Phenylpyrazoles from C(α)–Dianions of Carboalkoxyhydrazones and Phenylhydrazones," *J. Heterocyclic Chem. 24*:555–559, Hetero Corporation, Provo, Utah (1987).

Elguero, J. et al., "XIV.—Étude UV de pyrazoles," *Bulletin de la Société Chimique de France* (12):3744–3752, Société Chimique de France, Paris, France (1966).

Jacquier, R. and Maury, G., "(Dinitro–2', 4' phényl)–1 pyrazoles dérivant de l'hydroxyméthylène–2 cycloheptanone et de l'hydroxyméthyléne–3 camphre (Note de Laboratoire)," *Bulletin de la Société Chimique de France* (1):295–297, Société Chimique de France, Paris, France (1967).

Jacquier, R. and Maury, G., "XVII.—Synthèses et étude des (dinitro–2',4' phényl)–1 pyrazoles isomères dérivant d'acétyl–2 cyclanones (Première partie)," *Bulletin de la Société Chimique de France* (1):306–315, Société Chimiques de France, Paris, France (1967).

Jacquier, R. and Maury, G., "XIX.—Synthèses et étude des (dinitro–2',4' phényl(–1 pyrazoles isomères dérivant d'acétyl–2 cyclanones (Deuxième partie)," *Bulletin de la Société Chimique de France* (1):316–320, Société Chimique de France, Paris, France (1967).

Lyga, J.W. et al., "Synthesis, Mechanism of Action, and QSAR of Herbidical 3–Substituted–2–aryl–4,5,6,7–tetrahydroindazoles," *Pestic. Sci 42*:29–36, John Wiley & Sons, Inc., New York, NY (1994).

Malik, O.P. et al., "Synthesis of 2,3–Substituted 4,5,6, 7–Tetrahydro–2H–Indazoles; 2,4,5,6,7,8–Hexahydrocyclohepta(C) Pyrazoles and Their ω–t–Aminoalkyl Enol Ethers," *Harayana agric. Univ. J. Res. 10*:218–221 (1980).

Schenone, S. et al., "2–Aryl–3–Phenylamino–4, 5–Dihydro–2H–Benz[g]indazoles with Antiarrhythmic and Local Anaesthetic Activities," *Il Farmaco 50*: 179–182, Società Chimica Italiana, Rome, Italy (1995).

Strakova, I.A. et al., "Synthesis and Reactions of 1–(2–Pyridyl)–3–Methyl–4–Chloro–5–Formyl–6, 7–Dihydroindazoles," *Chem. Heterocyclic Compounds 34*:669–673, Plenum Publishing Corporation, London, England (1998).

Wang, Q. et al., "On the Reaction of 1–Aza–azoniaallene Salts with Acetylenes," *Chem. Ber. 127*:541–547, VCH Verlagsgesellschaft mbH, Weinheim, Germany (1994).

Williams, R.P. et al., "Synthesis and Alkylation of Tetrahydrocyclopentapyrazolols," *J. Med. Chem. 13*:773–775, American Chemical Society, Washington, DC (1970).

Yoichi, I., "Phenylpyrazole Derivative and Noxious Life Controlling Agent," *Patent Abstracts of Japan,* Publication No. 05262741, European Patent Office (1993).

Yukiaki, M., "Aminopyrazole Derivative, Its Production and Use," *Patent Abstracts of Japan,* Publication No. 08208620, European Patent Office (1996).

Yukiaki, M. "Pyrazole Derivative, Its Use," *Patent Abstracts of Japan,* Publication No. 08311036, European Patent Office (1996).

Dialog File 351, Accession No. 1662172, Derwent WPI English language abstract for FR 2,301,250 (Document AO5) (No date available).

CAPLUS Accession No. 1967:473550, Document No. 67:73550, CAPLUS English language abstract, American Chemical Society, Washington, DC, for Document AS5, Bardou, L. et al., *Bulletin de la Société Chimique de France* (1):289–294, Société Chimique de France, Paris, France (1967).

Dialog File 351, Accession No. 4501508, Derwent WPI English language abstract for JP 60–233061 (Document AM6) (No date).

Dialog File 351, Accession No. 4732434, Derwent WPI English language abstract for JP 61–165373 (Document AN6) (No date available).

Dialog File 351, Accession No. 7746781, Derwent WPI English language abstract for JP 63–287766 (Document AO6) (No date available).

Dialog File 351, Accession No. 9588344, Derwent WPI English language abstract for EP 0 558 999 A2 (Document AP6) (No date available).

CAPLUS Accession No. 1967:80664, Document No. 66:80664, CAPLUS English language abstract, American Chemical Society, Washington, DC, for Document AS7, Elguero, J. et al., *Bulletin de la Société Chimique de France* (12):3744–3752, Société Chimique de France, Paris, France (1966).

CAPLUS Accession No. 1967:403028, Document No. 67:3028, CAPLUS English language abstract, American Chemical Society, Washington DC, for Document AT7, Jacquier, R. and Maury, G., *Bulletin de la Société Chimique de France* (1):295–297, Société Chimique de France, Paris, France (1967).

CAPLUS Accession No. 1967:508588, Document No. 67:108588, CAPLUS English language abstract, American Chemical Society, Washington, DC, for Document AR8, Jacquier, R. and Maury, G., *Bulletin de la Société Chimique de France* (1):306–315, Société Chimique de France, Paris, France (1967).

CAPLUS Accession No. 1967:473551, Document No. 67:73551, CAPLUS English language abstract, American Chemical Society, Washington, DC, for Document AS8, Jacquier, R. and Maury, G., *Bulletin de la Société* Chimique de France (1):316–320, Société Chimique de France, Paris (1967).

Dialog File 351, Accession No. 12565980, Derwent WPI English language abstract for DE 197 56 115 A1 (Document AL8) (No date available).

USE OF 1,3-SUBSTITUTED PYRAZOL-5-YL SULFONATES AS PESTICIDES

This application claims benefit under 35 U.S.C. §119(e) of U.S. Provisional Application No. 60/141,849, filed Jul. 1, 1999.

BACKGROUND OF THE INVENTION

1. Field of the Invention

The present invention is in the field of substituted 1-arylpyrazole sulfonate compounds, their synthesis and their use as pest GABA receptor inhibitors and pesticides.

2. Related Art

γ-Aminobutyric acid (GABA) receptors are intrinsic membrane glycoproteins in vertebrate and invertebrate neuronal tissues that are members of the ligand-gated ion channel superfamily of receptors. GABA receptors play a major role in the inhibition of central nervous system (CNS) neuronal activity due to the widespread distribution of GABA-releasing and GABA-receptive neurons.

Vertebrate GABA receptors can be divided into two major classes: the $GABA_A$ and $GABA_C$ subtypes, and $GABA_B$ receptor subtype, which are distinguished by differences in their effector mechanisms and pharmacology (Knapp, R. J., et al., Neurochem. Res. 15:105–112 (1990)). $GABA_A$ and $GABA_C$ receptors are transmitter-operated chloride channels that are activated by GABA to open their chloride channel while $GABA_B$ receptors are thought to mediate changes in cyclic AMP levels through the activation of phospholipase activity (Eldefrawi, A. T. and Eldefrawi, M. E., FASEB J. 1:262–271 (1987); Knapp, R. J., et al., Neurochem. Res. 15:105–112 (1990)). The $GABA_A$ receptor and its associated chloride ion channel make up the so-called $GABA_A$ receptor-channel complex.

GABA is the endogenous ligand for the $GABA_A$ receptor of the $GABA_A$-complex, and is the major inhibitory neurotransmitter in the vertebrate brain, in the insect CNS and at insect neuromuscular junctions (Enna et al., In: Benzodiazepine/GABA Receptors and Chloride Channels: Structural and Functional Properties, Alan R. Liss, Inc., New York, pp. 41–56 (1986); Sattelle, D. B., Adv. Insect Physiol. 22:1–113 (1990)). GABA binding to its receptor stimulates chloride ion conductance through the associated chloride ion channel to inhibit synaptic transmission (Knapp, R. J., et al., Neurochem. Res. 15:105–112 (1990); U.S. Pat. No. 5,487,976). When two molecules of GABA bind at sites on the receptor, the chloride channel undergoes a conformational change and opens, allowing chloride ions to flow passively down the electrochemical gradient into the neuron. An influx of chloride into the cell causes a change in the membrane potential, usually a hyperpolarization, which results in an inhibition of the nerve impulse. Blockage of the GABA-gated chloride channel reduces neuronal inhibition, which leads to hyper-excitation of the CNS, resulting in convulsions and death. In contrast, irreversible or hyperactivation of the channel suppresses neuronal activity, resulting in ataxia, paralysis, coma and death (Bloomquist, J. R., Comp. Biochem. Physiol. 106C:301–314 (1993)).

$GABA_A$ receptors belong to the class 1 family of neurotransmitter/hormone receptors. Other class 1 members include the glycine receptor, the serotonin type-3 receptor, the nicotinic acetylcholine receptors (muscle and neuronal types) and several excitatory amino acid receptors of vertebrates. Class 1 receptors employ no second messengers and are found where a fast conductance is required. In contrast to class 1 receptors, class 2 receptors (e.g. muscarinic, adrenergic, and others) are coupled to a second messenger and/or a G protein for their transduction, with the channel involved being separate (and usually distant) from the receptor, which is both an agonist-binding and G protein-binding molecule (Barnard, E. A., et al., TiNS 10:502–509 (1987)).

$GABA_A$ receptors are pentameric oligomers, of about 250 kilodaltons (kDa), composed of six different types of subunits, α, β, γ, δ, ε and ρ, each of approximately 50 kDa (Olsen, R. W., and Tobin, A. J., FASEB J. 4:1469–1480 (1990); Hevers, W., and Lüddens, H., Mol. Neurobiol. 18:35–86 (1998)). Each subunit comprises a large extracellular N-terminal domain that putatively includes the ligand-binding site, four hydrophobic presumed membrane-spanning domains, one or more of which contribute to the wall of the ion channel, and a small extracellular C-terminus (Lüddens, H., and Wisden, W., TiPS 12:49–51 (1991); Olsen, R. W., and Tobin, A. J., FASEB J. 4:1469–1480 (1990); Hevers, W., and Lüddens, H., Mol. Neurobiol. 18:35–86 (1998)). Heterologous expression in vitro of different combinations of GABA receptor subunit types (α, β, γ, δ etc.) and subunit isoforms (α1, α2, etc. except δ) results in heteromultimeric receptors with differing structure and pharmacology (Schofield, P. R., TiPS 10:476–478 (1989); Burt et al., FASEB J. 5:2916–2923 (1991)).

GABA receptors also play an important role in the chemical control of pests, particularly insects, such as fleas, ticks, house flies, fruit flies, plant bugs, boll weevils, grasshoppers, cockroaches, mosquitoes, beetles, locust and moths (Hainzl, D., et al., Chem. Res. Toxicol. 11:1529–1535 (1998)). To date, all insect GABA receptors studied gate a fast acting chloride ion conductance. Although they appear to share many of the properties of $GABA_A$-type receptors in the vertebrate CNS, the majority of receptors in the insect nervous system appear to be bicuculline-, pitrazepin- and RU5135-insensitive (Anthony, N. M., et al., Comp. Mol. Neurobiol., Pichon, Y., ed., Birkhäuser Verlag, Basel, Switzerland, pp. 172–209 (1993); Wafford, K. A., et al., J. Neurochem. 48:177–180 (1987)). These findings indicate that insect GABA receptors contain several drug binding sites with structural and target site specificities that are different from vertebrate receptor-binding sites (Hainzl, D., et al., Chem. Res. Toxicol. 11:1529–1535 (1998)). Selective insecticides, e.g. insecticides with favorable selective toxicity for insects relative to vertebrates, are based in part on this target-site specificity between the GABA receptors of insects and the $GABA_A$ receptors of vertebrates (Moffat, A. S., Science 261:550–551 (1993); Hainzl, D., et al., Chem. Res. Toxicol. 11:1529–1535 (1998)).

Radiolabeled ligand binding studies have considerably expanded our knowledge of insect GABA receptor pharmacology. Within the insect GABA receptor three distinct binding sites have been identified: the GABA receptor agonist binding site, a benzodiazepine binding site and a convulsant binding site (Lummis, S. C. R., Comp. Biochem. Physiol. 95C:1–8 (1990); Rauh, J. J., et al., TiPS 11:325–329 (1990)). The convulsant binding site of GABA receptors in pests is the major target site for many of the drugs and pesticides currently on the market.

Convulsant drugs and pesticides act at the GABA receptor in pest brain, ganglia and muscle as noncompetitive blockers. Inhibition of GABA receptors in pests produces neurotoxicity (e.g. convulsions, paralysis, coma and death). In the early 1980s, the pesticides lindane and cyclodienes (e.g. dieldrin) were shown to antagonize the action of GABA in stimulating chloride uptake by various pest nerve and muscle preparations (Narahashi, T., Pharmacol. Toxicol. 78:1–14 (1996)). GABA receptors in pests are also blocked by picrotoxin, phenylpyrazole pesticides (e.g. Fipronil®), bicyclophosphorous esters (e.g. τ-butylbicyclophosphoronthionate), and bicycloorthobenzoates (4-n-propyl-4'-ethynylbicycloorthobenzoate) (U.S. Pat. No. 5,853,002). These pesticides block transmission of signals by GABA, and are very effective on a wide range of economically important pests.

Unfortunately, many potent pesticides and their derivatives also act at the $GABA_A$ receptors of animals. For example, fipronil sulfone and desulfinyl fipronil, a metabolite and photoproduct of fipronil, respectively, are not only toxic to pests, but also to upland game birds, freshwater fish and invertebrates, and waterfowl. In addition, fipronil itself is a toxicant for mammals even without oxidation to the sulfone (Hainzl, D., et al., *Chem. Res. Toxicol.* 11:1529–1535 (1998)).

Pesticides that effectively kill pests but that have little toxicity for animals and humans remain the aim of current research efforts. The present invention addresses the need for the development and use of new and more efficacious pesticides that are highly toxic to pests but not to animals susceptible to pest infestation.

SUMMARY OF THE INVENTION

A first aspect of the present invention is directed to a method of inhibiting a pest GABA receptor, comprising contacting a pest GABA receptor with a compound of Formula I.

A second aspect of the invention is directed to a method for controlling pests, comprising contacting an animal, plant or object with a composition comprising a pesticidally effective amount of at least one compound of Formula I, or a salt thereof, and one or more pesticidally-acceptable diluents or carriers.

A third aspect of the invention is pesticidal compositions comprising at least one compound of Formula I, or a salt thereof, and one or more pesticidally-acceptable diluents or carriers.

A fourth aspect of the present invention is directed to novel compounds of Formula I.

A fifth aspect of the present invention is directed to a method for synthesizing compounds of Formula I.

A sixth aspect of the invention is directed to the use of one or more compounds of Formula I for the manufacture of collars or external devices, as well as to a treatment process relating thereto.

DETAILED DESCRIPTION OF THE PREFERRED EMBODIMENTS

A first aspect of the present invention is directed to a method of inhibiting a pest GABA receptor, comprising contacting one or more pest GABA receptors with one or more compounds of Formula I:

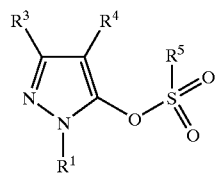

I or a salt thereof, wherein
$R^1$ is $C_{1-6}$ alkyl, $C_{6-14}$ aryl, or heteroaryl, any of which is optionally substituted;
$R^3$ is $C_{1-4}$ alkyl, $C_{1-4}$ alkoxy, $C_{1-4}$ alkylthio, $C_{1-4}$ alkylsulfinyl, or $C_{1-4}$ alkylsulfonyl, any of which is optionally substituted by one or more halogen atoms;
$R^4$ is hydrogen; and
$R^5$ is $C_{1-8}$ alkyl, $C_{3-7}$ cycloalkyl, $C_{3-7}$ cycloalkyl($C_{1-4}$) alkyl, $C_{6-14}$ aryl, $C_{6-14}$ ar($C_{1-4}$)alkyl, heteroaryl, heteroaryl ($C_{1-4}$)alkyl, any of which is optionally substituted.

A second aspect of the invention is directed to methods for controlling pests, comprising contacting an animal, plant or object with a composition comprising a pesticidally effective amount of at least one compound of Formula I, or a salt thereof, and one or more pesticidally-acceptable diluents or carriers. For purposes of the present invention, pests are undesired arthropods, in particular insects and arachnids, which are harmful to plants or animals susceptible to infestation by such arthropods. The methods of the present invention are suitable for combating animal pests, preferably arthropods, in particular insects and arachnids, encountered in and on companion animals, in agriculture, in forestry, in the protection of stored products and of materials, and in the hygiene field. Compounds employed in the methods of the invention have good plant tolerance or favorable safety to warm-blooded animals.

In particular, compounds of Formula I may be applied to control arthropods in compositions suitable for internal or external administration to vertebrates, or application for the control of arthropods in any indoor or outdoor area. Such compositions comprise at least one compound of Formula I and one or more diluents or carriers. The methods are more preferably used to reduce the viability and/or reproductive capacity of any ectoparasite. Preferred ectoparasites to target include arachnids, insects and leeches. More preferred ectoparasites include fleas and ticks. For example, the invention can be employed for killing fleas of the genus Ctenocephalides, in particular C. felis and C. canis, and ticks, in particular of the genus Rhipicephalus, especially R. sanguineus, as well as harvest ticks (Trombicula automnalis), Dermacentor variabilis, Dermacentor andersoni, Dermacentor occidentalis, Amblyomma americanum, Ixodes scapuris, and Ixodes pacificus.

A third aspect of the invention is directed to pesticidal compositions comprising a pesticidally effective amount of at least one compound of Formula I, or a salt thereof, and one or more pesticidally-acceptable diluents or carriers.

Preferred $R^1$ groups include $C_{1-6}$ alkyl and phenyl, either of which is optionally substituted by one or more halogen, hydroxy, methoxy or ethoxy. The phenyl groups can also be substituted by trifluoromethyl. Suitable values of $R^1$ include methyl, ethyl, phenyl, 2,4,6-trichlorophenyl, 2-6-dichloro-4-difluoromethoxyphenyl, 2-chloro-4-trifluoromethylphenyl, 2-bromo-4,6-di(trifluoromethyl) phenyl, 2,6-dibromo-4-trifluoromethylphenyl or 2-bromo-4-trifluoromethylphenyl. More preferably, $R^1$ is methyl or phenyl.

Preferred $R^3$ include $C_{1-4}$ alkyl, $C_{1-4}$ alkoxy, $C_{1-4}$ alkylthio, $C_{1-4}$ alkylsulfinyl, and $C_{1-4}$ alkylsulfonyl, any of which is optionally substituted by one or more halogen atoms. Suitable values include trifluoromethyl, methyl, methoxy, methylthio, methylsulfinyl, methylsulfonyl, ethylthio, ethylsulfinyl ethylsulfonyl, propylthio, —SCH$_2$CF$_3$, trifluoromethylthio and trifluoromethylsulfonyl.

R$^4$ is preferably hydrogen.

Preferred values of R$^5$ include C$_{1-8}$ alkyl, C$_{3-7}$ cycloalkyl, C$_{3-7}$ cycloalkyl(C$_{1-4}$)alkyl, and C$_{6-14}$ aryl, any of which is optionally substituted by one to five, preferably one to three of C$_{1-4}$ alkyl, C$_{1-4}$ alkoxy, C$_{1-4}$ alkylthio, hydroxy, amino, halo, and trifluoromethyl. Suitable values include methyl, ethyl, propyl, butyl, pentyl, cyclopentyl, cyclohexyl, cyclopropylmethyl, cyclopentylmethyl, cyclohexylmethyl, 2,4,6-trichlorophenyl, 2-6-dichloro-4-difluoromethoxyphenyl, 2-chloro-4-trifluoromethylphenyl, 2-chloro-4-fluorophenyl, 2,4-dichlorophenyl, 2-bromo-4,6-di(trifluoromethyl)phenyl, 2,6-dibromo-4-trifluoromethylphenyl or 2-bromo-4-trifluoromethylphenyl.

Most preferred compounds for use in compositions and methods of the present invention are those having the following structure:

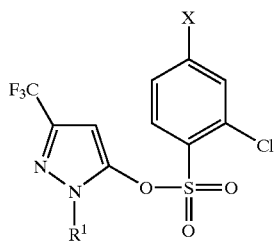

II where R$_1$ is methyl or phenyl, preferably methyl, and X is CF$_3$, Cl, or F.

Examples of suitable compounds are listed in Table 1. Preferred compounds include:

1-methyl-3-(trifluoromethyl)pyrazol-5-yl 2,4-dichlorobenzenesulfonate, 1-methyl-3-(trifluoromethyl)pyrazol-5-yl2-chloro4-fluorobenzenesulfonate, and 1-methyl-3-(trifluoromethyl)pyrazol-5-yl2-chloro-4-(trifluoromethyl) benzenesulfonate.

A fourth aspect of the invention is directed to compounds within the generic scope of Formula I that are novel. Such compounds include compounds of Formula I or salts thereof, wherein R$^1$ is C$_{1-6}$ alkyl, optionally substituted by one or more halogens; C$_{6-14}$ aryl, optionally substituted by one to five groups independently selected from the group consisting of halo (F, Cl, Br or I) trifluoromethyl, trichloromethyl, hydroxy, methoxy or ethoxy; or a C-attached heteroaryl group selected from the group consisting of pyridine, pyrazole, pyrrole, thiophene, furan, quinoline and benzofuran;

R$^3$ is C$_{1-4}$ alkyl, C$_{1-4}$ alkoxy, C$_{1-4}$ alkylthio, C$_{1-4}$ alkylsulfinyl, C$_{1-4}$ alkylsulfonyl, any of which is optionally substituted by one or more halogen atoms;

R$^4$ is hydrogen; and

R$^5$ is C$_{1-8}$ alkyl, C$_{3-7}$ cycloalkyl, C$_{3-7}$ cycloalkyl(C$_{1-4}$) alkyl, C$_{6-14}$ aryl, C$_{6-14}$ ar(C$_{1-4}$)alkyl, heteroaryl, heteroaryl(C$_{1-4}$)alkyl, any of which is optionally substituted.

Preferably, when R$^1$ is phenyl, then R$^5$ is a phenyl group having two or three substituents independently selected from the group consisting of halo and trifluoromethyl.

Preferred compounds in this aspect of the invention include compounds of Formula I, having the following values.

R$^1$ is C$_{1-6}$ alkyl, optionally substituted by one or more halogen, hydroxy, methoxy or ethoxy; or phenyl. Suitable values of R$^1$ include methyl, phenyl and ethyl. Most preferably, R$^1$ is methyl.

R$^3$ is C$_{1-4}$ alkyl, C$_{1-4}$ alkoxy, C$_{1-4}$ alkylthio, C$_{1-4}$ alkylsulfinyl, and C$_{1-4}$ alkylsulfonyl, any of which is optionally substituted by one or more halogen atoms. Suitable values of R$^3$ include trifluoromethyl, methyl, methoxy, methylthio, methylsulfinyl, methylsulfonyl, ethylthio, ethylsulfinyl ethylsulfonyl, propylthio, —SCH$_2$CF$_3$, trifluoromethylthio and trifluoromethylsulfonyl. Most preferably, R$^3$ is trifluoromethyl.

Preferred values of R$^5$ include C$_{1-8}$ alkyl, C$_{3-7}$ cycloalkyl, C$_{3-7}$ cycloalkyl(C$_{1-4}$)alkyl, and C$_{6-4}$ aryl, any of which is optionally substituted by one to five, preferably one to three of C$_{1-4}$ alkyl, C$_{1-4}$ alkoxy, C$_{1-4}$ alkylthio, hydroxy, amino, halo, and trifluoromethyl. Suitable values include methyl, ethyl, propyl, butyl, pentyl, cyclopentyl, cyclohexyl, cyclopropylmethyl, cyclopentylmethyl, cyclohexylmethyl, 2,4,6-trichlorophenyl, 2-6-dichloro-4-difluoromethoxyphenyl, 2-chloro-4-trifluoromethylphenyl, 2-chloro-4-fluorophenyl, 2,4-dichlorophenyl, 2-bromo-4,6-di(trifluoromethyl)phenyl, 2,6-dibromo-4-trifluoromethylphenyl or 2-bromo-4-trifluoromethylphenyl.

Most preferred compounds for use in compositions and methods of the present invention are those having Formula II:

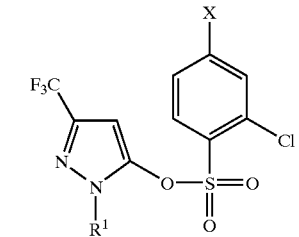

II where X is CF$_3$, Cl, or F.

A fifth aspect of the invention is directed to methods for synthesizing compounds of Formula I, comprising reacting a sulfonyl chloride with a substituted pyrazol-5-yl to form the sulfonate.

Sulfonyl chlorides of the formula R$^5$SO$_2$Cl (where R$^5$ is as defined above) are reacted with a substituted pyrazol-5-ol of the Formula III:

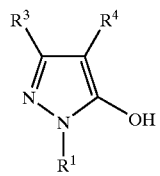

III where R$^1$, R$^3$ and R$^4$ are as defined immediately above to form a sulfonate of Formula I.

Definitions

The term "optionally substituted" when not otherwise explicitly provided for refers to the replacement of a hydrogen (or in the case of keto, two hydrogens) in a particular radical, with a functional group selected from the group consisting of halogen, trifluoromethyl, hydroxy, C$_{1-4}$ alkoxy, $C_{1-4}$ alkylthio, $C_{1-4}$ alkylsulfinyl, amino, nitro, cyano, $C_{2-6}$ carboxyalkyl, amidine, tetrazolyl, mono- or di-$(C_{1-6})$ alkylamino, mono- or di-$(C_{6-10})$arylamino, $C_{6-10}$ arylthio, $C_{6-10}$ arylsulfonyl, $C_{6-10}$ arylsulfinyl, oxime (N—OH), arylhydrazone, mono- and di-$(C_{1-6})$alkylaminocarbonyl, and mono-and di-$(C_{1-6})$alkylaminothiocarbonyl.

The term "alkyl" as employed herein by itself or as part of another group refers to both straight and branched chain radicals of up to 10 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, and decyl. Preferably, the alkyl chain is 2 to 8 carbon atoms in length, more preferably from 2 to 4 carbon atoms in length.

The term "alkenyl" is used herein to mean a straight or branched chain radical of 2–10 carbon atoms, unless the chain length is limited thereto, and having one or more double bonds, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length, more preferably, 2 to 4 carbon atoms in length.

The term "alkynyl" is used herein to mean a straight or branched chain radical of 2–10 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 8 carbon atoms in length, more preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl, tetrahydronaphthyl, or biphenyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "alkylthio" refers to any of the above alkyl groups linked to a sulfur atom.

The term "alkylsulfinyl" refers to any of the above alkyl groups linked to an —S(O)— group.

The term "alkylsulfonyl" refers to any of the above alkyl groups linked to an —SO$_2$— group.

The term "halogen" or "halo" as employed herein by itself or as part of another group refers to chlorine, bromine, fluorine or iodine with chlorine being preferred.

The term "heteroatom" is used herein to mean an oxygen atom ("O"), a sulfur atom ("S") or a nitrogen atom ("N"). It will be recognized that when the heteroatom is nitrogen, it may form an NRYZ moiety, wherein Ry and RZ are, independently from one another, hydrogen or $C_1$ to $C_8$ alkyl, or together with the nitrogen to which they are bound, form a saturated or unsaturated 5-, 6-, or 7-membered ring.

The term "salts with pesticidally-acceptable bases" means salts the cations of which are known and accepted in the art for the formation of salts of pesticidally active acids for agricultural, companion animal or horticultural use. When intended for application to vertebrates to combat infection or infestation by arthropods, the salts with bases used will be non-toxic. The term "non-toxic" means salts with bases the cations of which are innocuous to the vertebrates at the doses administered and which do not vitiate the beneficial effects produced by the anion.

Preferably, the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Where reference is made in the present specification to the compounds of Formula I such reference is intended to include also the salts with pesticidally-acceptable bases of compounds of Formula I where appropriate.

Compositions and Methods of Use

The compounds of Formula I can be employed as pesticides. For purposes of the present invention, pests are undesired arthropods, for example insects or arachnids, which are harmful to plants or animals susceptible to infestation by such arthropods.

Compounds of the invention are suitable for controlling animal pests, preferably arthropods, in particular insects and arachnids, encountered in and on companion animals, in agriculture, in forestry, in the protection of stored products and of materials, and in the hygiene field, and have good plant tolerance or favorable safety to warm-blooded animals.

Compounds of the invention while active against plant, hygiene and stored product pests, are particularly useful in the veterinary medicine sector, against animal ectoparasites such as scaly ticks, argasidae, scab mites, trombidae, flies (stinging and sucking), parasitic fly larvae, lice, hair lice, bird lice and fleas. For example, they have activity against fleas, such as fleas of the genus Ctenocephalides, in particular C. felis and C. canis, and ticks, such as ticks of the genus Rhipicephalus, especially R. sanguineus, as well as harvest ticks (Trombicula automnalis), Dermacentor variabilis, Dermacentor andersoni, Dermacentor occidentalis, Amblyomma americanum, Ixodes scapularis, and Ixodes pacificus. By virtue of their activity against fleas and ticks compounds of the invention are suitable for treating companion animals, such as dogs and cats.

Compounds of the invention are also suitable for the controlling of arthropods which infest useful animals in agriculture such as, for example, cattle, sheep, goats, horses, pigs, donkeys, camels, buffalo, rabbits, hens, turkeys, ducks, geese, bees, other domestic animals such as, for example, dogs, cats, cage birds, aquarium fish and so-called experimental animals such as, for example, hamsters, guinea pigs, rats and mice. The aim of combating these arthropods is to reduce fatalities and reductions in yield (in meat, milk, wool, skins, eggs, honey, etc.) so that the use of a compound according to the invention renders the keeping of animals more economic and more simple.

Compositions and methods of the present invention can be used to reduce the viability and/or reproductive capacity of any ectoparasite. Preferred ectoparasites to target include arachnids, insects and leeches. More preferred ectoparasites include fleas; ticks, including both hard ticks of the family Ixodidae (e.g., Ixodes and Amblyomma) and soft ticks of the family Argasidae (e.g., Ornithodoros, such as O. parkeri and O. turicata); flies, such as midges (e.g., Culicoides), mosquitos, sand flies, black flies, horse flies, horn flies, deer flies, tsetse flies, stable flies, myiasis-causing flies and biting gnats; ants; spiders; lice; mites; and true bugs, such as bed bugs and kissing bugs, including those carrying Chagas disease. Even more preferred ectoparasites include fleas, mosquitos, midges, sandflies, blackflies, ticks and kissing bugs, with fleas, ticks, mosquitos and midges being even more preferred.

Particularly preferred compositions and methods of the present invention targets fleas. Preferred fleas include Ctenocephalides, Xenopsylla, Pulex, Tunga, Nosopsyllus, Diamanus, Ctopsyllus and Echidnophaga fleas, with Ctenocephalides canis and Ctenocephalides felis fleas being even more preferred. For the purposes of illustration, many of the following embodiments discuss efficacy against fleas. Such discussion of efficacy against fleas is not intended, in any way, to limit the scope of the present invention.

A preferred aspect of the invention is directed towards killing fleas of the genus Ctenocephalides, in particular C. felis and C. canis, and ticks, in particular of the genus Rhipicephalus, especially R. sanguineus, as well as harvest ticks (Trombicula automnalis), Dermacentor variabilis, Dermacentor andersoni, Dermacentor occidentalis, Amblyomma americanum, Ixodes scapularis, and Ixodes pacificus.

An aspect of the present invention is also the use of a compound of Formula I for the production of a collar or other external device intended to be attached to a pet, in particular cats and dogs.

This aspect of the invention is directed mainly towards fleas of the genus Ctenocephalides, in particular C. felis and C. canis, and ticks, in particular of the genus Rhipicephalus, especially R. sanguineus, as well as harvest ticks (Trombicula automnalis), Dermacentor variabilis, Dermacentor andersoni, Dermacentor occidentalis, Amblyomma americanum, Ixodes scapularis, and Ixodes pacificus.

Collars intended to eliminate common ectoparasites from cats and dogs consist of a matrix, usually a plastic matrix, which incorporates between 5 and 40% active substance and is capable of releasing it over time.

Slow release compositions that can be in the form of a collar or earrings for controlling harmful insects are also contemplated. Such formulations comprise from about 0.5 to about 25% active material, from about 75 to about 99.5% of a suitable resin, such as polyvinyl chloride and a catalytic amount of a plasticizer, such as dioctyl phthalate.

A subject of the present invention is thus a collar or other external device for a pet, in particular a cat or dog, made of a matrix in which is incorporated from 0.1 to 40% by weight, relative to the collar, of a substance which is active against ectoparasites such as fleas and ticks (anti-flea and anti-tick collar or other external device), this active substance being formed of at least one compound corresponding to Formula I.

One aspect of this method is non-therapeutic and in particular relates to the cleaning of animal hairs and skin by elimination of the parasites which are present, as well as their residues and secretions. The treated animals thus have hair which is more pleasant to look at and to feel.

The invention also relates to such a method for therapeutic purposes, intended to treat and prevent parasitoses having pathogenic consequences.

Compounds of Formula I may be applied to control arthropods in compositions suitable for internal or external administration to vertebrates or application for the control of arthropods in any indoor or outdoor area. Such compositions comprise at least one compound of Formula I and one or more diluents or excipients. Such compositions can be prepared in any manner known in the art.

Suitable means of applying compounds of Formula I include:

to persons or animals infested by or exposed to infestation by arthropods by parenteral, oral or topical application. Examples include incorporation of an active compound in feed or suitable orally-ingestible pharmaceutical formulations, edible baits, salt licks, dietary supplements, pour-on and spot-on formulations, sprays, baths, dips, showers, jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their feces;

to growing crops as foliar sprays, dusts, granules, fogs and foams; also as suspensions of finely divided and encapsulated compounds of Formula I;

as soil and root treatments by liquid drenches, dusts, granules, smokes and foams; and as seed dressings by liquid slurries and dusts.

Compositions suitable for administration to vertebrates include preparations suitable for oral, parenteral, percutaneous, e.g. pour-on, spot-on or other topical administration.

Compositions for oral administration comprise one or more of the compounds of Formula I in association with non-toxic veterinary carriers or coatings and include, for example, chewable treats, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable veterinary vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or spot-on or pour-on preparations. Compounds of Formula I can also be administered with the aid of shaped articles which contain active compound, such as neck bands, ear tags, tail tags, limb bands, halters, marking devices and the like devices (e.g. ear tags) attached externally to animals in such a way as to provide local or systemic arthropod control.

Solid or liquid baits suitable for controlling arthropods comprise one or more compounds of Formula I and a carrier or diluent which may include a food substance or some other substance to induce consumption by the arthropod.

Medicated feeds which comprise a compound of Formula I and arthropodicidally-acceptable salts thereof and an edible carrier or diluent form an additional feature of the present invention.

Liquid compositions include water miscible concentrates, emulsifiable concentrates, flowable suspensions, wettable or soluble powders containing one or more compounds of Formula I which may be used to treat substrates or sites infested or liable to infestation by arthropods including premises, outdoor or indoor storage or processing areas, containers or equipment and standing or running water.

Solid homogenous or heterogenous compositions containing one or more compounds of Formula I, for example granules, pellets, briquettes or capsules, may be used to treat standing or running water over a period of time. A similar effect may be achieved using trickle or intermittent feeds of water dispersible concentrates.

Compositions in the form of aerosols and aqueous or non-aqueous solutions or dispersions suitable for spraying, fogging and low-or ultra-low volume spraying may also be used.

The compositions of the invention, besides at least one compound of Formula I and, if appropriate, besides extenders and auxiliaries, may also comprise at least one surfactant (wetting, dispersing and emulsifying agents).

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl-and octylphenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of Formula I may take the form of solutions, suspensions and emulsions of the compounds of Formula I optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of Formula I may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of Formula I which may be applied to control arthropod pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavouring agents, dyes and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with, the compositions of the present invention are: chlorpyrifos, demeton-S-methyl, disulfoton, ethoprofos, fenitrothion, malathion, parathion, triazophos, amitraz, cypermethrin, deltamethrin, fenpropathrin, fenvalerate, permethrin, aldicarb, carbosulfan, pirimicarb, bendiocarb, teflubenzuron, dicofol, endosulfan, lindane, benzoximate, avermectins, ivermectin, milbemycins, thiophanate, trichlorfon, dichlorvos, diaveridine and dimetridazole.

A "pesticidally effective amount" refers to an amount of compound that will be toxic to one or more pests under the conditions administered. When administered to vertebrates parenterally, orally or by percutaneous or other means, the dosage of compounds of Formula I will depend upon the species, age and health of the vertebrate and upon the nature and degree of its actual or potential infestation by arthropod pest. Determination of optimal ranges of effective amounts of each component in a composition is within the skill of the art. A single dose of 0.1 to 100 mg, preferably 2.0 to 20.0 mg, per kg body weight of the animal per month or doses of 0.01 to 20.0 mg, preferably 0.1 to 5.0 mg, per kg body weight of the animal per day for sustained medication are generally suitable by oral, topical or parenteral administration. By use of sustained release formulations or devices, the daily doses required over a period of months may be combined and administered to animals on a single occasion.

Compounds are screened for GABA receptor inhibiting activity using in vitro assays that measure the ability of a test compound to bind to pest and/or mammal GABA receptors. These assays, exemplified herein in working Examples 4 and 5, employ membranes possessing active GABA receptors. Preferred compounds have selectivity towards arthropod GABA receptor versus mammalian GABA receptor. Immediately following is a description of methods for forming such membranes.

Preparation of Housefly Membranes Possessing Active GABA Receptors

Newly emerged houseflies (Musca domestica, available from Rincon-Vitova Insectaries, Inc., Ventura, Calif.) were sedated with carbon dioxide gas, collected in 50 mL polypropylene conical tubes, and immediately frozen by submersion in liquid nitrogen. Unless specified, all of the following work was performed at 0–4° C. After removal from liquid nitrogen, the tubes of frozen houseflies were shaken vigorously by hand to decapitate the houseflies. The decapitated houseflies were then passed through a #10 mesh tissue sieve to separate the heads, which went through the sieve, from the larger abdomen, thoraxes, and residual intact houseflies that did not pass through the sieve. Contaminating wings were removed by holding a vacuum nozzle approximately 4 cm above the heads, and contaminating legs were separated from the heads by passage through a #15 mesh screen. All remaining debris were removed from the pool of heads using forceps. The purified heads were collected in 50 mL polypropylene conical tubes and stored in liquid nitrogen until processed further.

About 13 g of purified housefly heads were suspended in about 65 mL of 10% sucrose buffer (10% sucrose (w/w) in 10 mM Tris, pH 7.5). The heads were homogenized for about 1 minute, using a Tissumizer™ homogenizer equipped with a SDT-100EN probe (available from Tekmar-Dohrmann, Cincinnati, Ohio) running at 70% of its maximum speed. The extract was further homogenized by about 5 passes through a 40 mL Dounce tissue grinder. The extract was then centrifuged at about 500×g for about 5 minutes to pellet large debris. The supernatant was collected; the pellet was washed with an additional 65 mL of 10% sucrose buffer and centrifuged at 500×g for about 5 minutes. The second supernatant was collected and combined with the first supernatant, and the pool was filtered through a 100 μ CellMicroSieve™ mesh to remove residual debris (available from BioDesign of New York, Carmel, N.Y.).

Neuronal membranes containing active GABA receptors were collected via sucrose density centrifugation by the following method. About 8 mL of 35% sucrose buffer (35% sucrose (w/w) in 10 mM Tris, pH 7.5), were dispensed into each of six 38 mL ultracentrifuge tubes. These layers were overlaid with about 8 mL of 20% sucrose buffer (20% sucrose (w/w) in 10 mM Tris, pH 7.5), and finally overlaid with about 20 mL of filtered extract supernatant. The tubes were centrifuged at about 120,000×g for about 100 min at 4° C. After centrifugation, the 10% sucrose layer and most of the 20% sucrose layer were removed by aspiration. The membranes at the interface of the 20% sucrose and 35% sucrose layers were collected, pooled, diluted with 10% sucrose buffer, and centrifuged at about 120,000×g for about 40 min at 4° C. After centrifugation, the supernatant was discarded, and the pellets resuspended in about 6.5 mL of assay buffer (10 mM phosphate, 300 mM NaCl, pH 7.5) using a 10 mL Potter-Elvehjem tissue grinder with a Teflon® pestle. Protein concentration was determined by the Bio-Rad Protein Assay (available from Bio-Rad Laboratories, Hercules, Calif.) using bovine serum albumin as a standard. The membranes were aliquoted and stored in liquid nitrogen for up to 2 months before use.

Preparation of Mouse Brain Membranes Possessing Active GABA Receptors

Mouse brains were obtained from carbon dioxide-asphyxiated Swiss-Webster mice, washed with phosphate-buffered saline, and used either fresh or after storage at −80° C. for up to 10 months. Unless specified, all preparation steps were performed at 0–4° C. For each preparation, 20 brains were suspended in about 40 mL of 0.32 M sucrose and homogenized for about 2 minutes, using a Tissumizer™ homogenizer equipped with a SDT-100EN probe (available from Tekmar-Dohrmann, Cincinnati, Ohio) running at 50% of its maximum speed. The extract was centrifuged for about 5 min at about 1000×g to pellet intact brain tissue. The supernatant was retained and the pellet washed with an additional 40 mL of 0.32 M sucrose and centrifuged at 1000×g for about 5 minutes. The 1000×g supernatants were combined and centrifuged at about 10,000×g for about 20 min to pellet membranes. The 10,000×g supernatant was discarded and the pellet was resuspended in about 20 mL of water containing 1 mM EDTA. The sample was dialyzed two times for about 3 hours each against about 3 L of water. The sample was then centrifuged at about 25,000×g for about 30 min to pellet the membranes. After centrifugation, the supernatant was discarded and the pellet recovered. The protein concentration of the pellet was determined by the Bio-Rad Protein Assay (available from Bio-Rad Laboratories, Hercules, Calif.) using bovine serum albumin as a standard. The membranes were aliquoted and stored at −80° C. for up to 6 months before use.

Preparation of Compounds

The present invention is also directed to methods for forming compounds of Formula I, comprising reacting a sulfonyl chloride with a substituted pyrazol-5-yl to form the sulfonate. Sulfonyl chlorides of the formula $R^5SO_2Cl$ (where $R^5$ is as defined above) are reacted with a substituted pyrazol-5-ol of Formula III:

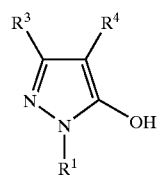

III were $R^1$, $R^3$ and $R^4$ are as defined immediately above to form a sulfonate of Formula I.

Compounds of Formula I can be prepared according to the general synthetic scheme shown below, where $R^1$-$R^5$ are as described above. Pyrazole starting materials are either commercially available or can be readily synthesized by condensation between a substituted hydrazine and a β-ketoester employing conditions known to those of skill in the art. The reaction can be run in a suitable solvent such as anhydrous pyridine, dichloromethane, or chloroform at a temperature of between about −78° C. to about 30° C.

The included examples are illustrative, but not limiting, of the compounds, methods and compositions of the present invention. Other suitable modifications and adaptations of the variety of conditions and parameters normally encountered and obvious to those skilled in the art are within the spirit and scope of the invention.

EXAMPLE 1

1-methyl-3-(trifluoromethyl)pyrazol-5-yl 2,4-dichlorobenzenesulfonate 2,4-Dichlorobenzenesulfonyl chloride (245 mg, 1.0 mmol) was added in portions to an ice-cold solution of 1-methyl-3-(trifluoromethyl)pyrazol-5-ol (166 mg, 1.0 mmol) in anhydrous pyridine (5 mL). The resulting solution was stirred at room temperature overnight, and poured onto ice-water. The mixture obtained is stirred for 1 h, and the precipitate formed filtered, yielding 244 mg (65% yield) of the desired product. NMR (δ, CDCl$_3$): 8.0 (1H, d, J=8.5 Hz); 7.65 (1H, d, J=2.1 Hz); 7.4 (1H, dd, J=8.5; 2.1 Hz); 6.1 (1H, s); 3.9 (s, 3H).

EXAMPLE 2

1-methyl-3-(trifluoromethyl)pyrazol-5-yl 2-chloro-4-fluorobenzenesulfonate

Using a similar procedure, this compound was obtained in 50% yield.

NMR (δ, CDCl$_3$): 8.1 (1H, dd, J=5.6; 8.9 Hz); 7.4 (1H, dd, J=2.5; 8.1 Hz); 7.1 (1H, m); 6.1 (1H, s); 3.9 (s, 3H).

EXAMPLE 3

1-methyl-3-(trifluoromethyl)pyrazol-5-yl 2-chloro-4-(trifluoromethyl)benzenesulfonate Using a similar procedure, this compound was obtained in 50% yield. NMR (δ, CDCl$_3$): 8.2 (1H, d, J=8.6 Hz); 7.9 (1H, d, J=2.8 Hz); 7.4 (1H, dd, J=8.6; 2.8 Hz); 6.1 (1H, s); 3.9 (s, 3H).

EXAMPLE 4

In Vitro Assay to Screen Compounds for Ability to Bind Housefly GABA Receptors Housefly neuronal membranes were prepared as described above from housefly heads. Test compounds were dissolved in dimethylsulfoxide (DMSO) at concentrations ranging from about 2 nM to about 100 mM. About 1 μL of a dissolved test compound was dispensed into a well of a 96-well polystyrene plate. About 100 μL of ice cold assay buffer (10 mM phosphate, 300 mM NaCl, pH 7.5) containing 5.2 nM 4'-Ethynyl-4-n-[2,3-$^3$H$_2$] propylbicycloorthobenzoate ($^3$H-EBOB, 38 Ci/mmol, available from NEN Life Science Products, Boston, Mass.) was added to the well, followed by about 100 μL of ice cold assay buffer containing about 0.5–1.0 mg/mL housefly neuronal membranes. Control wells were prepared the same way except that the housefly neuronal membranes were omitted from the "negative" wells, and the test compounds were omitted from the "positive" wells. The samples were incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat was air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding was considered to be the difference between total $^3$H bound to the neuronal membranes in the absence of any inhibitors and nonspecific $^3$H bound to the neuronal membranes upon the addition of 5 μM unlabeled EBOB. The average radioactivity contained in the "negative" wells was subtracted from each of the assay wells. The results indicated that about 60-90% of the $^3$H-EBOB bound to the housefly neuronal membranes in the absence of inhibitors was specifically bound. Compounds that displaced $^3$H-EBOB at a level equivalent to 5 μM unlabeled EBOB were said to display "100% inhibition" of $^3$H-EBOB binding, while compounds that did not displace $^3$H-EBOB at all were said to display "0% inhibition" of $^3$H-EBOB binding. Compounds that displaced $^3$H-EBOB specifically bound to the housefly neuronal membranes were tested at 24–48 different final concentrations, varying from about 0.1 nM to about 125 μM, in order to determine the concentration at which 50% of the maximum inhibition due to the addition of that compound was observed (IC$_{50}$). This value was calculated by plotting the data on a log-linear plot and either dropping a line to the x-axis perpendicular to a line drawn to the y-axis at approximately 50% inhibition of $^3$H-EBOB binding, or by fitting the data to the formula I=XY/(X+Z), in which I is the percent inhibition of $^3$H-EBOB binding, X is the inhibitor concentration, Y is the maximum percent inhibition of $^3$H-EBOB binding observed, and Z is the calculated IC$_{50}$.

Compounds of the present invention had the activities listed in Table 1 in this assay.

TABLE 1

| Cmpd. No. | R$^1$ | R$^3$ | R$^4$ | R$^5$ | Fly IC$_{50}$ (μM) | Mouse IC$_{50}$ (μM) |
|---|---|---|---|---|---|---|
| 1 | CH$_3$ | CF$_3$ | H | 2,4,5-trichlorophenyl | 1.6 | 8.4 |
| 2 | CH$_3$ | CF$_3$ | H | 3,4-dichlorophenyl | 1.7 | 9. |
| 3 | CH$_3$ | CF$_3$ | H | 2,5-dichlorophenyl | 5.0 | 2. |
| 4 | CH$_3$ | CF$_3$ | H | 3-chlorophenyl | 10. | 0.5 |
| 5 | CH$_3$ | CF$_3$ | H | 2-chloro-4-trifluoromethylphenyl | 0.49 | 14. |
| 6 | CH$_3$ | CF$_3$ | H | 3,4-dibromophenyl | 5.0 | 12.5 |
| 7 | CH$_3$ | CF$_3$ | H | 4-chloro-3-methylphenyl | 20. | 11. |
| 8 | CH$_3$ | CF$_3$ | H | 3-fluorophenyl | 8.8 | 0.16 |
| 9 | CH$_3$ | CF$_3$ | H | 2,6-difluorophenyl | 20. | 6. |
| 10 | CH$_3$ | CF$_3$ | H | 3,4-difluorophenyl | 5.0 | 1. |
| 11 | CH$_3$ | CF$_3$ | H | 4-fluoro-2-methylphenyl | 23. | 3.6 |
| 12 | CH$_3$ | CF$_3$ | H | 2,4-dichlorophenyl | 0.90 | 4.9 |
| 13 | CH$_3$ | CF$_3$ | H | naphth-2-yl | 15. | 3. |
| 14 | phenyl | CF$_3$ | H | 3-chloro-4-fluorophenyl | 3.0 | 12. |
| 15 | phenyl | CF$_3$ | H | 3,4-dichlorophenyl | 100. | NI* |
| 16 | CH$_3$ | CF$_3$ | H | 3-chloro-2-methylphenyl | 30. | 12. |
| 17 | CH$_3$ | t-butyl | H | 2,4-dichlorophenyl | 7.0 | 5.4 |
| 18 | phenyl | CH$_3$ | Cl | 2-chloro-4-fluorophenyl | 2.0 | 1.0 |
| 19 | CH$_3$ | t-butyl | H | 2-chloro-4-fluorophenyl | 0.42 | 1.3 |
| 20 | CH$_3$ | CF$_3$ | H | 2-chloro-4-fluorophenyl | 1.0 | 3.3 |

*NI = non-inhibitor

Compounds of Examples 1, 2 and 3 were the most active with IC$_{50}$ values ranging from about 0.5 to about 1 μM.

EXAMPLE 1

In Vitro Assay to Screen Compounds for their Ability to Bind Mouse Brain GABA Receptors Mouse brain membranes were prepared as described above from dissected mouse brains. Test compounds were dissolved in dimethylsulfoxide (DMSO) at concentrations ranging from about 2 nM to about 100 mM. About 1 μL of a dissolved test compound was dispensed into a well of a 96-well polystyrene plate. About 100 μL of ice cold assay buffer (10 mM phosphate, 300 mM NaCl, pH 7.5) containing 5.2 nM 4'-Ethynyl-4-n-[2,3-$^3$H$_2$] propylbicycloorthobenzoate ($^3$H-EBOB, 38 Ci/mmol, available from NEN Life Science Products, Boston, Mass.) was added to the well, followed by about 100 μL of ice cold assay buffer containing about 0.25–0.5 mg/ml mouse brain membranes. Control wells were prepared the same way except that the mouse brain membranes were omitted from the "negative" wells, and the test compounds were omitted from the "positive" wells. The samples were incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.).

The filtermat was air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding was considered to be the difference between total $^3$H bound to the mouse brain membranes in the absence of any inhibitors and nonspecific $^3$H bound to the mouse brain membranes upon the addition of 5 $\mu$M unlabeled EBOB. The average radioactivity contained in the "negative" wells was subtracted from each of the assay wells. The results indicated that about 80–95% of the $^3$H-EBOB bound to the mouse brain membranes in the absence of inhibitors was specifically bound. Compounds that displaced $^3$H-EBOB at a level equivalent to 5 $\mu$M unlabeled EBOB were said to display "100% inhibition" of $^3$H-EBOB binding, while compounds that did not displace $^3$H-EBOB at all were said to display "0% inhibition" of $^3$H-EBOB binding. Compounds that displaced $^3$H-EBOB specifically bound to the mouse brain membranes were tested at 24–48 different final concentrations, varying from about 1 nM to about 125 $\mu$M, in order to determine the concentration at which 50% of the maximum inhibition due to the addition of that compound was observed (IC$_{50}$). This value was calculated by plotting the data on a log-linear plot and either dropping a line to the x-axis perpendicular to a line drawn to the y-axis at approximately 50% inhibition of $^3$H-EBOB binding, or by fitting the data to the formula I=XY/(X+Z), in which I is the percent inhibition of $^3$H-EBOB binding, X is the inhibitor concentration, Y is the maximum percent inhibition of $^3$H-EBOB binding observed, and Z is the calculated IC$_{50}$.

The results indicated that the compounds of Examples 1, 2 and 3 had IC$_{50}$ values ranging from about 3.3 to about 14 $\mu$M.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of inhibiting a pest GABA receptor, comprising contacting one or more pest GABA receptors with one or more compounds of Formula I:

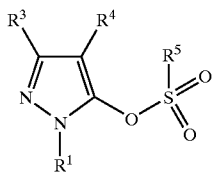

I or a salt thereof, wherein:
R$^1$ is C$_{1-6}$ alkyl or phenyl, either of which is optionally substituted with one or more of groups independently selected from the group consisting of halogen, hydroxy, methoxy and ethoxy;
R$^3$ is C$_{1-4}$ alkyl, C$_{1-4}$ alkoxy, C$_{1-4}$ alkylthio, C$_{1-4}$ alkylsulfinyl or C$_{14}$ alkylsulfonyl, any of which is optionally substituted by one or more halogen atoms;
R$^4$ is hydrogen; and
R$^5$ is C$_{1-8}$ alkyl, C$_{3-7}$ cycloalkyl, C$_{3-7}$ cycloalkyl(C$_{1-4}$) alkyl, or C$_{6-14}$ aryl, any of which is optionally substituted by one to five substituents independently selected from the group consisting of C$_{1-4}$ alkyl, C$_{1-4}$ alkoxy, C$_{1-4}$ alkylthio, hydroxy, amino, halo, and trifluoromethyl.

2. A method for controlling pests, comprising contacting a vertebrate animal, plant or inanimate object with a pesticidally effective amount of at least one compound of Formula I:

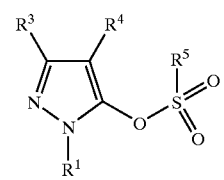

I or a salt thereof, wherein
R$^1$ is C$_{1-6}$ alkyl or phenyl, either of which is optionally substituted with one or more groups independently selected from the group consisting of halogen, hydroxy, methoxy and ethoxy;
R$^3$ is C$_{1-4}$ alkyl, C$_{1-4}$ alkoxy, C$_{1-4}$ alkylthio, C$_{1-4}$ alkylsulfinyl or C$_{1-4}$ alkylsulfonyl, any of which is optionally substituted by one or more halogen atoms;
R$^4$ is hydrogen; and
R$^5$ is C$_{1-8}$ alkyl, C$_{3-7}$ cycloalkyl, C$_{3-7}$ cycloalkyl(C$_{1-4}$) alkyl, or C$_{6-14}$ aryl, any of which is optionally substituted by one to five substituents independently selected from the group consisting of C$_{1-4}$ alkyl, C$_{1-4}$ alkoxy, C$_{1-4}$ alkylthio, hydroxy, amino, halo, and trifluoromethyl.

3. The method of claim 1, wherein R$^1$ is methyl, ethyl, 2,4,6-trichlorophenyl, 2-6-dichloro-4-difluoromethoxyphenyl, 2-chloro-4-trifluoromethylphenyl, 2-bromo-4,6-di(trifluoromethyl)phenyl, 2,6-dibromo-4-trifluoromethylphenyl or 2-bromo-4-trifluoromethylphenyl.

4. The method of claim 1, wherein R$^1$ is methyl.

5. The method of claim 1, wherein R$^3$ is trifluoromethyl, methyl, methoxy, methylthio, methylsulfinyl, methylsulfonyl, ethylthio, ethylsulfinyl ethylsulfonyl, propylthio, —SCH$_2$CF$_3$, trifluoromethylthio or trifluoromethylsulfonyl.

6. The method of claim 1, wherein R$^5$ is methyl, ethyl, propyl, butyl, pentyl, cyclopentyl, cyclohexyl, cyclopropylmethyl, cyclopentylmethyl, cyclohexylmethyl, 2,4,6-trichlorophenyl, 2-6-dichloro-4-difluoromethoxyphenyl, 2-chloro-4-trifluoromethylphenyl, 2-chloro-4-fluorophenyl, 2,4-dichlorophenyl, 2-bromo-4,6-di(trifluoromethyl)phenyl, 2,6-dibromo-4-trifluoromethylphenyl or 2-bromo-4-trifluoromethylphenyl.

7. The method of claim 1, wherein R$^5$ is 2-chloro-4-trifluoromethylphenyl, 2-chloro-4-fluorophenyl, or 2,4-dichlorophenyl.

8. The method of claim 1, wherein R$^1$ is methyl, R$^3$ is trifluoromethyl, R$^4$ is hydrogen and R$^5$ is 2-chloro-4-trifluoromethylphenyl, 2-chloro-4-fluorophenyl, or 2,4-dichlorophenyl.

9. The method of claim 2, wherein R$^1$ is methyl, R$^3$ is trifluoromethyl, R$^4$ is hydrogen and R$^5$ is 2-chloro-4-trifluoromethylphenyl, 2-chloro-4-fluorophenyl, or 2,4-dichlorophenyl.

10. The method of claim 2, wherein said pests are insects, arachnids, leeches or any combination thereof.

11. The method of claim 1, wherein R$^1$ is C$_{1-6}$ optionally substituted alkyl; R$^3$ is C$_{1-4}$ alkyl optionally substituted by one or more halogens; $R^4$ is hydrogen; and $R^5$ is optionally substituted $C_{6-14}$ aryl.

12. The method of claim 2, wherein $R^1$ is methyl, ethyl, 2,4,6-trichlorophenyl, 2-6-dichloro-4-difluoromethoxyphenyl, 2-chloro-4-trifluoromethylphenyl, 2-bromo -4,6 -di(trifluoromethyl)phenyl, 2,6-dibromo-4-trifluoromethylphenyl or 2-bromo-4-trifluoromethylphenyl.

13. The method of claim 2, wherein $R^1$ is methyl.

14. The method of claim 2, wherein $R^3$ is trifluoromethyl, methyl, methoxy, methylthio, methylsulfinyl, methylsulfonyl, ethylthio, ethylsulfinyl ethylsulfonyl, propylthio, —$SCH_2CF_3$, trifluoromethylthio or trifluoromethylsulfonyl.

15. The method of claim 2, wherein $R^5$ is methyl, ethyl, propyl, butyl, pentyl, cyclopentyl, cyclohexyl, cyclopropylmethyl, cyclopentylmethyl, cyclohexylmethyl, 2,4,6-trichlorophenyl, 2-6-dichloro-4-difluoromethoxyphenyl, 2-chloro-4-trifluoromethylphenyl, 2-chloro-4-fluorophenyl, 2,4-dichlorophenyl, 2-bromo-4,6-di(trifluoromethyl)phenyl, 2,6-dibromo-4-trifluoromethylphenyl or 2-bromo-4-trifluoromethylphenyl.

16. The method of claim 2, wherein $R^5$ is 2-chloro-4-trifluoromethylphenyl, 2-chloro-4-fluorophenyl, or 2,4-dichlorophenyl.

17. The method of claim 2, wherein $R^1$ is methyl, $R^3$ is trifluoromethyl, $R^4$ is hydrogen and $R^5$ is 2-chloro-4-trifluoromethylphenyl, 2-chloro-4-fluorophenyl, or 2,4-dichlorophenyl.

* * * * *